United States Patent [19]

Mohacsi

[11] E Re. 30,452

[45] Reissued Dec. 16, 1980

[54] 3-PHENOXYMORPHINANS AND DERIVATIVES THEREOF

[75] Inventor: Ernest Mohacsi, Nutley, N.J.

[73] Assignee: Hoffmann-La Roche Inc., Nutley, N.J.

[21] Appl. No.: 85,072

[22] Filed: Oct. 15, 1979

Related U.S. Patent Documents

Reissue of:

[64] Patent No.: 4,113,729
Issued: Sep. 12, 1978
Appl. No.: 811,233
Filed: Jun. 29, 1977

U.S. Applications:

[63] Continuation-in-part of Ser. No. 748,022, Dec. 6, 1976, abandoned.

[51] Int. Cl.[3] ..... C07D 221/28; C07D 217/18; A61K 31/485

[52] U.S. Cl. ..... 546/74; 546/149; 424/260

[58] Field of Search ..... 546/74; 424/260

[56] References Cited

FOREIGN PATENT DOCUMENTS 2030981 1/1971 Fed. Rep. of Germany .

OTHER PUBLICATIONS

Sawa et al., Chemical Abstracts, vol. 62, 11788g–11789c (1965).

*Primary Examiner*—Donald G. Daus
*Assistant Examiner*—Diana G. Rivers
*Attorney, Agent, or Firm*—Jon S. Saxe; George M. Gould; William H. Epstein

[57] ABSTRACT

Levo-rotary 3-phenoxy N-substituted morphinans and derivatives thereof useful as analgesics and/or narcotic antagonists and their preparation form (-)-3-hydroxy-N-lower alkyl morphinan including intermediates in this preparation.

18 Claims, No Drawings

3-PHENOXYMORPHINANS AND DERIVATIVES THEREOF

Matter enclosed in heavy brackets [ ] appears in the original patent but forms no part of this reissue specification; matter printed in italics indicates the additions made by reissue.

BACKGROUND OF THE INVENTION

This application is a continuation-in-part of U.S. Pat. application Ser. No. 748,022 filed Dec. 6, 1976, now abandoned.

SUMMARY OF THE INVENTION

In accordance with this invention, it has been discovered that compounds of the formula:

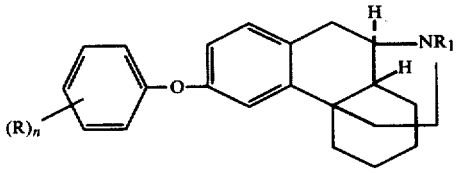

I wherein R is halo, nitro, lower alkyl, lower alkoxy or hydrogen; $R_1$ is hydrogen, lower alkyl, lower alkenyl, $—CH_2(CH_2)_pR_2$ and $$—\overset{O}{\overset{\|}{C}}—(CH_2)_pR_2;$$

$R_2$ is heteroaromatic, aromatic or cyclo-lower alkyl; p is an integer from 0 to 3; and n is an integer from 1 to 5 and pharmaceutically acceptable salts thereof are useful as pain killing analgesics and/or narcotic antagonists.

In accordance with this invention, the compound of formula I can be prepared from a compound of the formula

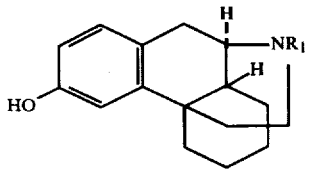

II wherein $R_1$ is as above.

DETAILED DESCRIPTION OF THE INVENTION

As used herein, the term "halogen" includes all four halogens, i.e., bromine, chlorine, fluorine and iodine with fluorine and bromine being preferred. The term "lower alkyl" includes both straight and branched chain saturated aliphatic hydrocarbon groups containing from 1 to 7 carbon atoms, i.e., methyl, ethyl, n-propyl, isopropyl, n-butyl, isobutyl, etc., with methyl being preferred. The term "lower alkenyl" designates both straight and branched chain aliphatic hydrocarbon groups containing from 2 to 7 carbon atoms which contain one olefinic double bond such as vinyl, allyl, prop-2-en-1-yl, etc. The preferred lower alkenyl groups are $—CH_2—CH=CH_2$, $$—CH_2—CH=\overset{CH_3}{\overset{|}{C}}—CH_3 \text{ and } —CH_2—\overset{CH_3}{\overset{|}{C}}=CH_2.$$

The term "cyclo-lower alkyl" designates saturated cyclic aliphatic hydrocarbon groups containing a ring of from 3 to 6 carbon atoms. Among the preferred cyclo-lower alkyl groups are cyclopropyl, cyclobutyl and cyclohexyl. The term "lower alkoxy" designates lower alkoxy groups containing from 1 to 7 carbon atoms such as methoxy, ethoxy, propoxy, isopropoxy, etc.

The term "heteroaromatic" designates hydrocarbon ring systems containing a hetero atom selected from the group consisting of oxygen, nitrogen, or sulfur and having 5 or 6 members in the ring structure. Among the preferred heteroaromatic ring structures are included thienyl, pyrolyl, furyl, pyridyl, pyranyl, etc.

The compound of formula I is prepared from the compound of formula II by reacting the compound of formula II with a compound of the formula

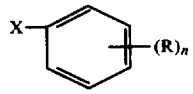

III wherein R and n are as above; and X is halogen. The compounds of formula II and III are reacted to form the compound of formula I utilizing a copper catalyst. This reaction is carried out in an organic solvent in the presence of an inorganic alkali metal base. In carrying out this reaction, any conventional organic solvent can be utilized. Among the preferred solvents are nitrobenzene, collidine, diglime and tertiary amines. Among the tertiary amines are included the cyclic tertiary amines such as pyridine and the tri-lower alkyl amines such as trimethyl amine, triethyl amine, etc. This reaction is also carried out in the presence of an inorganic base, such as an alkali metal base. Among the preferred bases are included the alkali metal hydroxides such as potassium and sodium hydroxide as well as the alkali metal carbonates and bicarbonates such as sodium carbonate, potassium carbonate, sodium bicarbonate and potassium bicarbonate. The preferred inorganic base for utilization in this invention is a weak base such as potassium carbonate. In carrying out this reaction, temperature and pressure are not critical and this reaction can be carried out at room temperature and atmospheric pressure. However, if desired, elevated temperatures can be utilized. Generally, it is preferred to utilize temperatures of from 100°-250° C. in carrying out this reaction. This reaction takes place in the presence of a copper catalyst such as cupric chloride, cupric bromide, cupric sulfate, cuprous iodide, a mixture of copper-bronze and metalic copper, with granual copper being preferred.

Where R in the compound of formula I is a hydroxy group, the reaction of the compound of formula II with the compound of formula III in the aforementioned manner produces the compound of formula I where R is hydroxy in poor yields. Therefore, it is preferred to prepare this compound according to another means. This is accomplished by utilizing a compound of formula I where R is lower alkoxy as a starting material, i.e. a compound of the formula

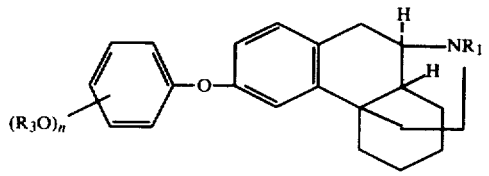

I-A wherein n, $R_1$ are as above; and $R_3$ is lower alkyl. By utilizing the compound of formula I-A as a starting material, a compound of the formula:

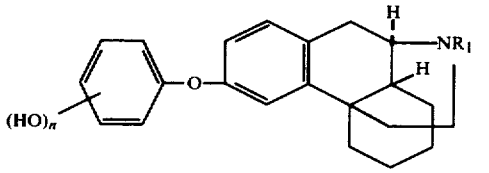

I-B is produced.

The compound of formula I-A is converted to the compound of formula I-B by ether cleavage. Any conventional method of ether cleavage can be utilized. Among the preferred methods is by treating the compound of formula I-A with potassium hydroxide in diglyme or by treating the compound of formula I-A with pyriding hydrochloride or aqueous hydrogen bromide in acetic acid. Any of the conditions conventional in ether cleavage can be utilized to convert the compound of formula I-A to I-B. It should be noted that ether cleavage does not cleave the phenoxy group. Therefore, the phenoxy group cannot be cleaved from the compound of formula I to produce a material which would be an addicting narcotic.

Where $R_1$ in the compound of formula I is methyl, i.e. a compound of the formula:

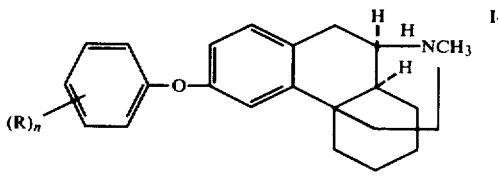

I-C where n and R are as above. This compound can be converted in accordance with another embodiment of this invention to a compound of the formula:

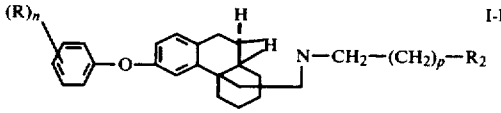

I-D wherein R, $R_2$, p and n are as abovve; or a compound of the formula:

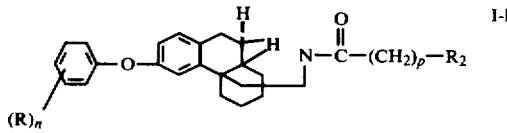

I-E

In the conversion of the compound of formula I-C to I-D, the compound of formula I-E is formed as an intermediate. In forming the compound of formula I-E, the compound of formula I-C is reacted with a compound of the formula:

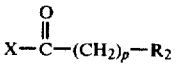

IV wherein $R_2$, p and X are as above. This reaction is carried out by refluxing in the presence of an inert organic solvent. Any conventional aromatic solvent can be used in this reaction. Among the preferred are the aromatic hydrocarbon solvents such as benzene or toluene. If, desired, the compound of formula I-E can be converted to the compound of formula I-D by treatment with an aluminum hydride reducing agent such as an alkali metal aluminum hydride, i.e. lithium aluminum hydride or a di(lower alkyl) aluminum hydride such as diisobutyl aluminum hydride. Any of the conditions conventional in utilizing these aluminum hydride reducing agents can be utilized to carry out this reduction.

In accordance with another embodiment of this invention, the compound of formula I-D can be prepared from the compound of formula I-C via the following intermediates:

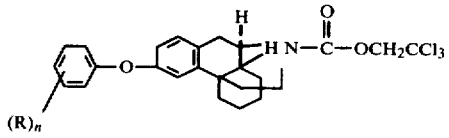

VI wherein R and n are as above

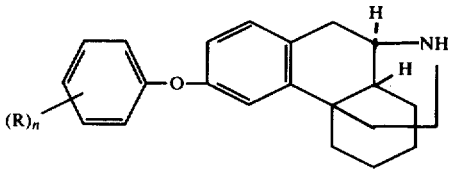

VII wherein R and n are as above.

The compound of formula I-C is converted to the compound of formula VI by treating the compound of formula I-C with trichloroethyl chloroformate. In carrying out this rection, any inert organic solvent can be utilized as the organic solvent. Among the preferred solvents are the aromatic hydrocarbon solvents such as benzene, toluene, etc. Generally, this reaction is carried out in the presence of a weak base. Any of the conventional weak inorganic bases can be utilized in this reaction. Among the preferred weak bases are the alkali metal carbonates and bicarbonates such as potassium or sodium carbonate. In carrying out this reaction, temperature and pressure are not critical and this reaction can be carried out at room temperature or atmospheric pressure. On the other hand, elevated temperatures and pressures can be utilized. Generally, it is preferred to carry out this reaction at the reflux temperature of the reaction medium.

The compound of formula VI is converted to the compound of formula VII by treatment with zinc in a lower alkanoic acid. The lower alkanoic acid serves as the solvent medium for this reaction. Any conventional lower alkanoic acids such as acetic acid, propionic acid, etc., can be utilized. In carrying out this reaction, temperature and pressure are not critical and this reaction can be carried out at room temperature and atmospheric pressure. On the other hand, temperatures as high as 100° C. can be utilized to carry out this reaction.

In accordance with another embodiment of this invention, the compound of formula I-C can be converted to the compound of formula VII via any procedure for dialkylation. Any conventional dialkylating agent and procedure can be utilized to convert the compound of formula I-C to the compound of formula VII. Among the dialkylating agents which can be utilized in this reaction are included cyanogen bromide followed by treatment with an inorganic mineral acid or ethyl or phenyl chloroformate ester followed by treatment with an alkali metal hydroxide in a lower alkanol. Any of the conditions conventional in utilizing these di-alkylating agents can be utilized to affect the conversion of a compound of formula I-C to a compound of formula VII. The compound of formula VII can be converted to the compound of formula I-D by reacting the compound of formula VII with a compound of the formula $$X—CH_2—(CH_2)_p—R_2 \qquad X$$

where X, $R_2$ and p are as above.

The compound of the formula VII is reacted with the compound of the formula X to produce the compound of formula I-D in a organic polar solvent medium utilizing a temperature of from 120° C. to 300° C. In carrying out this reaction, any polar solvent having a boiling point of from 120° C. to 300° C. can be utilized. Among the preferred solvents are included the high boiling polar solvents such as dimethyl sulfoxide, dimethyl formamide. This reaction is carried out in the presence of an inorganic alkali metal base. Any conventional inorganic alkali metal base, such as sodium bicarbonate, potassium carbonate, sodium carbonate can be utilized in this reaction. Generally, it is preferred to utilize weak organic bases such as sodium or potassium bicarbonate or carbonate. In carrying out this reaction, temperature and pressure are not critical and this reaction can be carried out at room temperature or atmospheric pressure. Generally, it is preferred to carry out this reaction under reflux conditions.

In accordance with another embodiment of this invention, the compound of formula VII is converted to the compound of formula I-E by reaction with a compound of formula IV. This reaction is carried out in an inert polar organic solvent. Any conventional polar solvent can be utilized. Among the preferred organic polar solvents are included benzene, toluene, methylene chloride. This reaction is carried in the presence of an organic base such as triethylamine, pyridine and the like. In carrying out this reaction, temperature and pressure are not critical and the reaction can be carried out at room temperature or elevated temperatures.

In accordance with another embodiment of the invention, the compound of formula VII can be converted to a compound of the formula

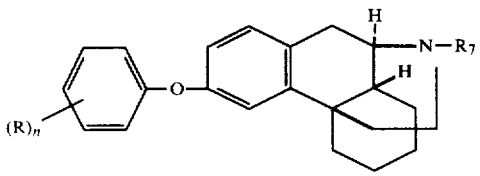

I-G wherein R and n are as above; and $R_7$ is lower alkyl, or lower alkenyl by reaction with a compound of the formula $$X—R_7$$

where X and $R_7$ are as above. This reaction is carried out by the same procedure as described in connection with the reaction of a compound VII with a compound of the formula X to produce a compound of the formula I-D.

In accordance with another embodiment of this invention, the compound of formula I can be prepared from a compound of the formula

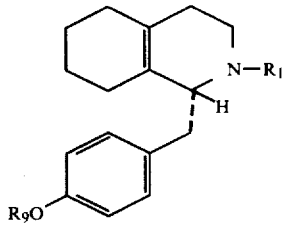

XI wherein $R_1$ is as above and $R_9$ is lower alkyl via the following intermediates

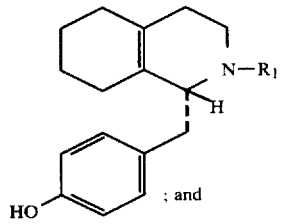

XII

; and

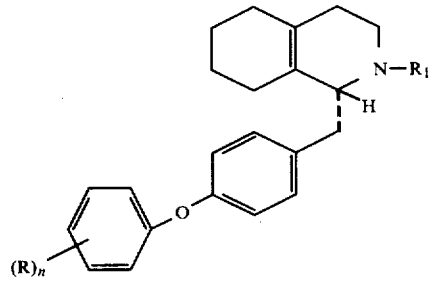

XIII wherein R, $R_1$ and n are as above.

In converting the compound of formula XI to the compound of formula XII, ether cleavage is utilized. Any conventional method of ether cleavage can be utilized to carry out this conversion. Among the preferred methods is to treat the compound of formula XI with alkali metal hydroxides such as sodium or potassium hydroxide in an ether solvent such as diglime. Generally, this reaction is carried out at the reflux temperature of the reaction medium. The compound of formula XII is converted to the compound of formula XIII by reacting the compound of formula XII with a compound of formula III. This reaction is carried out in the same manner as described in connection with the reaction of the compound of formula II with a compound of formula III to produce the compound of formula I.

The compound of formula XIII is converted to the compound of formula I by cyclization. This cyclization is carried out by treating the compound of formula XIII with a strong mineral acid. Any conventional strong mineral acid can be utilized such as phosphoric acid, sulfuric acid, hydrochloric acid, with phosphoric acid being preferred. The inorganic acid can be utilized as the solvent medium. In carrying out this reaction, temperature and pressure are not critical and this reaction can be carried out at room temperature and atmospheric pressure. On the other hand, temperatures as high as 250° C. can be utilized. Generally, it is preferred to carry out this reaction with a temperature of from 100°-200° C.

The compounds of formula I above form pharmaceutically acceptable acid addition salts with inorganic acids. Thus, the compounds of the present invention form pharmaceutically acceptable acid addition salts with inorganic acids such as hydrochloric acid, hydrobromic acid, sulfuric acid and phosphoric acid; and with organic acids such as tartaric acid, oxalic acid, citric acid, camphorsulfonic acid, ethanesulfonic acid, toluenesulfonic acid, salicylic acid, ascorbic acid, maleic acid, succinic acid, formic acid, acetic acid and the like.

The compounds of formula I and their pharmaceutically acceptable salts are useful as analgesics and/or as narcotic antagonists. These compounds, when administered orally or parentally, provide a relief from pain in the same manner as codeine. Furthermore, the compounds of this invention cannot be degraded chemically into compounds which have addiction liability such as dromoran.

The compounds of formula I and salts as herein described can be incorporated into standard pharmaceutical dosage forms, for example, they are useful for oral or parenteral application with the usual pharmaceutical adjuvant material, for example, organic or inorganic inert carrier materials such as water, gelatin, lactose, starch, magnesium stearate, talc, vegetable oils, gums, polyalkyleneglycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The daily dose administered for the compounds will of course vary with the particular novel compounds employed because of the very potency of the compounds, the chosen route of administration and the size of the recipient. The dosage administered is not subject to definite bounds but it will usually be in effective amounts of the pharmacological function of the compound of formula I. Representative of a typical method for administering the compounds of formula I is by the oral type administration route. By this route, a tablet containing the compound of formula I can be administered orally at the rate of 0.01 microgram to 0.15 microgram per day per kilogram of body weight.

The compounds of formula I above and their salts are used as analgesic pain killing agents. This analgesic activity can be demonstrated in the standard phenylquinone writhing test (Sigmund et al., Proc. Soc. Exp. Biol. Med. 95: 729 [1957]). The compounds of this invention significantly reduce pain and produce analgesic effects in mice exposed to intra-abdominally induced chemical pain. The $ED_{50}$ was the dose which reduced the total number of writhes by 50%. When the following compounds of formula I are utilized as the test substances, analgesic activity is observed as shown by the following $ED_{50}$ levels when compared to the standard analgesic agent codeine:

(—)-3-phenoxy-N-methylmorphinan tartrate—$ED_{50}$ 2.0 mg/kg (S.C.);

(—)-3-(p-methyl)phenoxy-N-methylmorphinan hydrochloride—$ED_{50}$ 23 mg/kg (s.c.);

[(—)-3-(p-methyl)phenoxy-N-methylmorphinan hydrochloride—$ED_{50}$ 2.0 mg/kg (s.c.);]

[(—)-3-phenoxy-N-cyclobutylmethylmorphinan hydrochloride—$ED_{50}$ 13.0 mg/kg (s.c.);]

[(—)-3-phenoxy-N-phenethylmorphinan oxalate—$ED_{50}$ 0.9 mg/kg (s.c.);]

[(—)-3-phenoxy-N-[2-(2-furyl)ethyl]morphinan oxalate—$ED_{50}$ 1.0 mg/kg (s.c.);]

[(—)-3-phenoxy-N-[2-(2-thienyl)ethyl]morphinan sulfate—$ED_{50}$ 13.0 mg/kg (s.c.);]

[(—)-3-(m-fluoro)phenoxy-N-methylmorphinan d-tartrate—$ED_{50}$ 6.0 mg/kg (s.c.);]

[(—)-3-(o-methoxy)phenoxy-N-cyclopropylmethylmorphinan hydrochloride—$ED_{50}$ 2.5 mg/kg (s.c.);]

[(—)-3-(p-methoxy)phenoxy-N-cyclopropylmethylmorphinan hydrochloride—$ED_{50}$ 1.3 mg/kg (s.c.);]

(—)-3-(m-Methoxy)phenoxy-N-methylmorphinan oxalate—$ED_{50}$ 2.5 mg/kg (s.c.).

(—)-3-(o-Methoxy)phenoxy-N-methylmorphinan oxalate—$ED_{50}$ 0.49 mg/kg (s.c.).

(—)-3-(p-Hydroxy)phenoxy-N-methylmorphinan hydrochloride—$ED_{50}$ 1.3 mg/kg (s.c.).

(—)-3-(m-Hydroxy)phenoxy-N-methylmorphinan d-tartrate—$ED_{50}$ 9.0 mg/kg (s.c.).

(—)-3-(o-Hydroxy)phenoxy-N-methylmorphinan d-tartrate—$ED_{50}$ 1.8 mg/kg (s.c.).

(—)-3-(o-Nitro)phenoxy-N-methylmorphinan hydrochloride—$ED_{50}$ 2.8 mg/kg (s.c.).

(—)-3-(p-Fluoro)phenoxy-N-methylmorphinan hydrochloride—$ED_{50}$ 1.0 mg/kg (s.c.).

(—)-3-(o-Fluoro)phenoxy-N-methylmorphinan oxalate—$ED_{50}$ 3.0 mg/kg (s.c.).

(—)-3-Pentafluorophenoxy-N-methylmorphinan oxalate—$ED_{50}$ 9.2 mg/kg (s.c.).

(—)-3-Phenoxy-N-cyclopropylmethylmorphinan hydrochloride(17)—$ED_{50}$ 1.7 mg/kg (s.c.). and Codeine—$ED_{50}$ 3.9 mg/kg (s.c.).

The compounds of formulae I above effectively counteract morphine analgesia. This activity can be demonstrated in the mice tail flick test for morphine antagonism. This test is used to measure narcotic antagonism. Compounds are given subcutaneously 10 minutes prior to morphine sulfate. The percent evaluation in reaction time was determined during each test for 10 mg/kg s.c. of morphine sulfate and actual percent increase was used in calculating the percent antagonism of morphine analgesia. The percent antagonism was calculated according to the formula of Harris and Pierson, J. Pharmacol. Exp. Ther., 143:141, 1964. When the following representative compound of the present invention was utilized as the test substance, morphine antagonism activity is obtained as shown by the following $ED_{50}$ level (—)-3-phenoxy-N-cyclopropylmethylmorphinan hydrochloride $ED_{50}$ 40.28 mg/kg (s.c.).

The term aromatic designates a hydrocarbon aromatic substituent such as phenyl, naphthyl with phenyl being preferred.

The following examples are illustrative but not limitative of the invention. All temperatures are in degrees Centigrade. The ether utilized is diethyl ether. Millimeters (mm) as used in the examples is mmHg of mercury.

EXAMPLE 1

(—)-3-Pentafluorophenoxy-N-methylmorphinan

A mixture of 6.0 g (0.023 mol) of (—)-3-hydroxy-N-methylmorphinan, 60 ml of freshly distilled pyridine, 4.8 g of potassium carbonate, 9.0 g of hexafluorobenzene, and 6.0 g of copper (granular) were heated in a stainless steel container at 120° C. for 7 days. After cooling, the container was opened and the mixture was filtered. The filtrate was concentrated under reduced pressure, and the residue was partitioned between ether (700 ml) and 5 N aqueous sodium hydroxide. After removal of ether, the residue was extracted with hexane (200 ml). The residue obtained from the hexane extract (5.0 g) was chromatographed over neutral alumina (75 g), eluted with methylene chloride, diethyl ether, and ethyl acetate. After the fractions were combined, the solvents were removed under reduced pressure to give 3.6 g (36%) of crude (—)-3-pentafluorophenoxy-N-methylmorphinan. For analysis, a sample of this compound was distilled, bp 150°-160°/0.1 mm, $[\alpha]^{25}$ D−39.69° (c 1.21, MeOH).

To the above base, 3.6 g (0.01 mol) in 20 ml of diethyl ether, a solution of 0.8 g of oxalic acid in 20 ml of ether was added. The crude oxalate was recrystallized from ethyl acetate to give 3.2 g (73%) of (—)-3-pentafluorophenoxy-N-methylmorphinan oxalate hemihydrate, m.p. 157°-160°, $[\alpha]^{25}$ D−24.50° (c 1.00, MeOH).

EXAMPLE 2

(—)-3-Phenoxy-N-methylmorphinan

A solution of 10.2 g (0.04 mol) of (—)-3-hydroxy-N-methylmorphinan in 240 ml of freshly distilled pyridine was refluxed with stirring under nitrogen with 18.5 g of bromobenzene, 13.8 g of potassium carbonate and 13.0 g of copper (granular) for 8 days. The mixture was filtered and the filtrate was concentrated under reduced pressure. The residue was partition between ether (500 ml) and 5 N aqueous sodium hydroxide (200 ml). The ether solution was washed with water and dried. After removal of ether, the residue was distilled, bp 180°-185°/0.1 mmHg to give 10.0 g (76%) of the base, i.e. (—)-3-phenoxy-N-methylmorphinan. A sample of this compound was recrystallized from ether, mp 87°-88°, $[\alpha]^{25}$ D−60.10° (c 1.01, MeOH).

To the above base, 10.0 g (0.03 mol) in 50 ml of ether, a solution of 3.2 g of oxalic acid in 100 ml of ether was added. The crude oxalate was recrystallized from ethanol to give 11.5 g (91%) of (—)-3-phenoxy-N-methylmorphinan oxalate, mp 184°-185° (d), $[\alpha]^{25}$ D−35.47° (c 1.00, MeOH).

To 7.0 g (0.02 mol) of base, in 25 ml of acetone with stirring, a warm solution of 3.5 g of d-tartaric acid in 75 ml of acetone was added. The mixture was stirred at room temperature for 0.5 hr, then at 0° to 5° for 4 hrs. The tartrate salt was separated by filtration and recrystallized from ethanol (40 ml) to give 10.0 g (98%) of pure (—)-3-phenoxy-N-methylmorphinan d-tartrate, mp 131°-133°, $[\alpha]^{25}$ D−20.08° (c 0.99, MeOH).

EXAMPLE 3

(—)-3-(p-Methyl)phenoxy-N-methylmorphinan

A solution of 5.0 g (0.019/0.15 mol) (—)-3-hydroxy-N-methylmorphinan in 20 ml of freshly distilled pyridine was refluxed with stirring under nitrogen with 6.4 g of p-bromotoluene, 4.0 g of potassium carbonate, and 0.2 g of copper (granular) for 9 days. The mixture was filtered and the filtrate was concentrated under reduced pressure. The residue was extracted with ether (200 ml) and the ether solution was washed with 2 N sodium hydroxide (100 ml), then water and dried. After removal of ether, the residue was distilled, bp 125°-140° 10.15 mmHg to give 3.9 g (58%) of (—)-3-(p-methyl)-phenoxy-N-methylmorphinan. A sample of this compound was crystallized from ether, mp 94°-96°, $[\alpha]^{25}$ D−55.98° (c 1.00, MeOH).

The above base, 3.3 g (0.01 mol), on treatment with hydrogen chloride (anhydrous) in ethyl acetate (5 ml), afforded 3.3 g of crude hydrochloride. Recrystallization from ethyl acetate gave 3.0 g (82%) of (—)-3-(p-methyl)phenoxy-N-methylmorphinan hydrochloride, mp 223°-224°, $[\alpha]^{25}$ D−37.85° (c 0.69, MeOH).

EXAMPLE 4

(—)-3-(p-Methoxy)phenoxy-N-methylmorphinan

A solution of 5.1 g (0.02 mol) of (—)-3-hydroxy-N-methylmorphinan in 20 ml of freshly distilled pyridine was refluxed with stirring under nitrogen with 7.5 g of p-bromoanisole, 4.01 g of potassium carbonate and 0.2 g of copper (granular) for 7 days. The mixture was filtered and the filtrate was concentrated under reduced pressure. The residue was partitioned between ether (400 ml) and 10 N sodium hydroxide (100 ml). The ether solution was washed with water and dried. After removal of ether, the residue was distilled, bp 139°-155°/0.15 mmHg to give 3.9 g (54%) of the product (—)-3-(p-methoxy)phenoxy-N-methylmorphinan. This compound was crystallized from ether to afford 3.3 g (46%) of pure product, mp 130°-132°, $[\alpha]^{25}$ D−51.59° (c 0.99, MeOH).

The above product, 2.0 g (0.006 mol) on treatment with hydrogen chloride (anhydrous) in ethyl acetate, afforded the crude hydrochloride salt of the product, which after crystallization from ethyl acetate gave 1.1 g (50%) of (—)-3-(p-methoxy)-phenoxy-N-methylmorphinan hydrochloride, mp 170°-172°, $[\alpha]^{25}$ D−34.22° (c 0.99, MeOH).

EXAMPLE 5

(—)-3-(m-Methoxy)phenoxy-N-methylmorphinan

A solution of 5.1 g (0.02 mol) of (—)-3-hydroxy-N-methylmorphinan in 20 ml of freshly distilled pyridine was refluxed with stirring under nitrogen with 7.5 g of m-bromoanisole, 4.1 g of potassium carbonate and 0.2 g of copper (granual) for 10 days. To the reaction mixture was added ether (twice the volume) and filtered. The filtrate was concentrated under reduced pressure and the residue was partitioned between ether and 5 N sodium hydroxide. The ether solution was washed with water and dried. After removal of ether, the residue was distilled, bp 145°-160°/0.1 mmHg to give 5.47 g (76%) of the product (—)-3-(m-methoxy)phenoxy-N-methylmorphinan. For analysis, a sample of this compound was crystallized from ether, mp. 88°-90°, $[\alpha]^{25}$ D−61.81° (c 1.00, MeOH).

To the above product, 1.5 g (0.004 mol), in ether, a solution of 0.4 g of oxalic acid in ether was added. The crude oxalate salt was recrystallized from ethanol-ether to give 1.7 g (91%) of (—)-3-(m-methoxy)phenoxy-N-methylmorphinan oxalate, mp 148°-150°, $[\alpha]^{25}$ D−39.60° (c 1.00, MeOH).

EXAMPLE 6

(—)-3-(o-Methoxy)phenoxy-N-methylmorphinan

A solution of 5.1 g (0.02 mol) of (—)-3-hydroxy-N-methylmorphinan in 20 ml of freshly distilled pyridine was refluxed with stirring under nitrogen with 7.5 g of o-bromoanisole, 4.1 g of potassium carbonate and 5.0 g of copper (granual) for 3 days. The mixture was filtered and the filtrate was concentrated under reduced pressure. The residue was partitioned between ether and 5 N sodium hydroxide. The ether solution was washed with water and dried. After removal of the solvent, the residue was distilled, bp 165°/0.2 mmHg to give 2.7 g (36%) of the product (—)-3-(o-methoxy)phenoxy-N-methylmorphinan. For analysis, a sample of this compound was crystallized from ethyl acetate, mp 87°-89°, $[\alpha]^{25}$ D−59.32° (c 1.16, MeOH).

To the above product, 2.7 g (0.01 mol), in ether a solution of 0.7 g of oxalic acid in ether was added. The crude oxalate salt was recrystallized from ethanol-ether to give 1.8 g (54%) of (—)-3-(o-methoxy)phenoxy-N-methylmorphinan oxalate, mp 185°-187° (d), $[\alpha]^{25}$ D—37.19° (c 0.99, MeOH).

EXAMPLE 7

(—)-3-(p-Hydroxy)phenoxy-N-methylmorphinan

A mixture of 2.0 g (0.005 mol) of (—)-3-(p-methoxy)-phenoxy-N-methylmorphinan and 20 g of pyridine hydrochloride was heated at 220° with stirring under nitrogen for 25 minutes, cooled in an ice bath, and diluted with water (50 ml). The mixture was made basic with conc. ammonium hydroxide and extracted with chloroform (100 ml). The chloroform solution was washed with water (50 ml) and dried. Removal of the solvent in vacuo gave a residue which was treated with ether and filtered to give 1.79 g (66%) of the product (—)-3-(p-hydroxy)phenoxy-N-methylmorphinan. For analysis, a sample of this compound was crystallized from ethanol-ether, mp 188°-190°, $[\alpha]^{25}$ D−51.6° (c 0.86, MeOH).

The above product, 1.4 g (0.004 mol) on treatment with hydrogen chloride (anhydrous) in ethyl acetate (10 ml), afforded the crude hydrochloride. Crystallization of this compound from ethanol-ethyl acetate gave 1.2 g (78%) of (—)-3-(p-hydroxy)phenoxy-N-methylmorphinan hydrochloride, mp 160°-163° (d), $[\alpha]^{25}$ D−34.55° (c 0.99, MeOH).

EXAMPLE 8

(—)-3-(m-Hydroxy)phenoxy-N-methylmorphinan

A mixture of 3.8 g (0.01 mol) of (—)-3-(m-methoxy)-phenoxy-N-methylmorphinan and 30 g of pyridine hydrochloride was heated at 220° with stirring under nitrogen for 25 minutes, cooled in an ice bath and diluted with water. The mixture was made basic with conc. ammonium hydroxide and extracted with ether. The ether extracts were washed with water and dried. Removal of the solvent in vacuo gave 3.2 g (88%) of the product (—)-3-(m-hydroxy)phenoxy-N-methylmorphinan. For analysis, a sample of this compound was recrystallized from ethanol, mp 212°-214°, $[\alpha]^{25}$ D−53.13° (c 1.00, MeOH).

To the above product 2.2 g (0.01 mole), in ethanol, a solution of 1.0 g of di-tartaric acid in ethanol (20 ml) was added. The solution was diluted with ether and the crystals were collected. The crude salt was recrystallized from ethanol-ethyl acetate to give 2.8 g (81%) of (—)-3-(m-hydroxy)phenoxy-N-methylmorphinan d-tartrate ethanolate, mp 135°-138°, $[\alpha]^{25}$ D−19.21° (c 1.26, MeOH).

EXAMPLE 9

(—)-3-(o-Hydroxy)phenoxy-N-methylmorphinan

A mixture of 2.5 g (0.007 mol) of (—)-3-(o-methoxy)-phenoxy-N-methylmorphinan and 25.0 g of pyridine hydrochloride was heated at 220° with stirring under nitrogen for 25 minutes, cooled in an ice bath and diluted with water (50 ml). The mixture was made basic with conc. aqueous ammonium hydroxide and extracted with chloroform (80 ml). The chloroform solution was washed with water and dried. Removal of the solvent in vacuo gave the crude base, which after crystallization from ethyl acetate-hexane afforded 1.5 g (63%) of pure product (—)-3-(o-hydroxy)-phenoxy-N-methylmorphinan, mp 167°-168°, $[\alpha]^{25}$ D−52.91° (c 1.07, MeOH).

The above product, 0.152 g (0.001 mol) and 0.07 g of d-tartaric acid were dissolved in 1 ml of hot ethanol and allowed to crystallize at room temperature. The crude salt was recrystallized from ethanol to give 0.222 g (94%) of (—)-3-(o-hydroxy)phenoxy-N-methylmorphinan d-tartrate ethanolate, mp 111°-112°, $[\alpha]^{25}$ D−15.96° (c 1.07, MeOH).

EXAMPLE 10

(—)-3-(o-Nitro)phenoxy-N-methylmorphinan

A solution of 6.4 g (0.02 mol) of (—)-3-hydroxy-N-methylmorphinan in 30 ml of freshly distilled pyridine was refluxed with stirring under nitrogen with 10.0 g of 1-bromo-2-nitrobenzene, 6.0 g of potassium carbonate and 0.3 g of copper (granual) for 3 days. The mixture was filtered and the filtrate was concentrated under reduced pressure. The residue was partitioned between ether and 5 N sodium hydroxide. The ether solution was washed with water and dried. The ether was removed and the residue was partitioned again between chloroform and 5 N sodium hydroxide. After removal of chloroform in vacuo, the residue was crystallized from ether to give 2.1 g (22%) of the product (—)-3-(o-nitro)phenoxy-N-methylmorphinan, mp 158°-160°, $[\alpha]^{25}$ D−53.16° (c 0.99, MeOH).

The above product, 2.0 g (0.005 mol), on treatment with hydrogen chloride (anhydrous) in ethyl acetate, afforded the crude hydrochloride, which after crystallization from ethyl acetate gave 1.2 g (54%) of (—)-3-(o-nitro)phenoxy-N-methylmorphinan hydrochloride hemihydrate, mp 155°-157° (d), $[\alpha]^{25}$ D−32.62° (c 0.99, MeOH).

EXAMPLE 11

(—)-3-(p-Fluoro)phenoxy-N-methylmorphinan

A solution of 5.1 g (0.02 mol) of (—)-3-hydroxy-N-methylmorphinan in 20 ml of freshly distilled pyridine was refluxed with stirring under nitrogen with 17.0 g of p-fluoro-bromobenzene, 4.1 g of potassium carbonate and 0.2 g of copper (granual) for 5 days. To the reaction mixture, ether (twice the volume) was added and filtered. The filtrate was concentrated in vacuo, and the residue was suspended in 150 ml of hot hexane and filtered. The filtrate was washed with 5 N sodium hydroxide then water and dried. After removal of the solvent, the residue was crystallized from hexane to give 4.5 g (65%) of the product (—)-3-(p-fluoro)-phenoxy-N-methylmorphinan, mp 102°-104°, $[\alpha]^{25}$ D−53.36° (c 1.00, MeOH).

The above product, 4.0 g (0.01 mol), on treatment with hydrogen chloride (anhydrous) in ethyl acetate, afforded the crude hydrochloride. Recrystallization from ethyl acetate gave 4.0 g (89%) of (—)-3-(p-fluoro)-phenoxy-N-methylmorphinan hydrochloride hemihydrate, mp 162°-164°, $[\alpha]^{25}$ D−34.83° (c 0.98, MeOH).

EXAMPLE 12

(—)-3-(o-Fluoro)phenoxy-N-methylmorphinan

A solution of 2.0 g (0.007 mol) of (—)-3-hydroxy-N-methylmorphinan in 10 ml of freshly distilled pyridine was refluxed with stirring under nitrogen with 3.5 g of o-fluorobromobenzene, 2.0 g of potassium carbonate and 2.0 g of copper (granual) for 2 days. To the reaction mixture, ether (twice the volume) was added and filtered. The filtrate was concentrated in vacuo and the residue was taken up in ether (200 ml) and washed with 5 N sodium hydroxide. The ether solution was washed with water and dried. Removal of ether gave 2.5 g (92%) of crude product (—)-3-(o-fluoro)phenoxy-N-methylmorphinan. For analysis, a sample of this compound was crystallized from ether, mp 113°-115°, $[\alpha]^{25}$ D−48.67° (c 0.95, MeOH).

To the above product 2.5 g (0.007 mol), in ether a solution of 0.7 g oxalic acid in ether (25 ml) was added. The crude oxalate salt was recrystallized from ethanol to give 2.4 g (77%) of (—)-3-(o-fluoro)phenoxy-N-methylmorphinan oxalate, mp 180°-182°, $[\alpha]^{25}$ D−30.98° (c 1.00, MeOH).

EXAMPLE 13

(—)-3-Phenoxy-N-trichlorocarbethoxymorphinan

To a mixture of 2.3 g (0.007 mol) of (—)-3-phenoxy-N-methylmorphinan, 150 ml of benzene and 0.35 g of potassium carbonate was added dropwise, 3.3 g of 2,2,2-trichloroethyl chloroformate. The reaction mixture was stirred at reflux for 6 days. The mixture was diluted with ether and extracted with 4 N hydrochloride acid. The organic phase was washed with dilute ammonium hydroxide, water, and dried. Removal of solvent gave 3.4 g (99%) of the product (—)-3-phenoxy-N-trichlorocarbethoxymorphinan. For analysis, a sample of this compound was distilled, bp 230°-240°/0.05 mmHg, $[\alpha]^{25}$ D−119.65° (c 0.95, MeOH).

EXAMPLE 14

(—)-3-Phenoxymorphinan

To a solution of 3.4 g (0.007 mol) of (—)-3-phenoxy-N-trichlorocarbethoxymorphinan in 40 ml of 90% acetic acid was added portionwise 2.0 g of zinc-dust. The mixture was stirred at room temperature for 16 hours and filtered. The filtrate was concentrated in vacuo and the residue was partitioned between ether and dilute ammonium hydroxide. The ether solution was extracted with 4 N hydrochloric acid. The acidic solution was extracted with chloroform. After removal of chloroform, the crude hydrochloride was crystallized from ethanol to afford 0.7 g (29%) of (—)-3-phenoxymorphinan hydrochloride, mp 322°-324°, $[\alpha]^{25}$ D−33.88° (c 1.00, MeOH).

EXAMPLE 15

(—)-3-Phenoxy-17-cyclopropylcarbonylmorphinan

To a solution of 3.7 g (0.011 mol) of (—)-3-phenoxy-N-methylmorphinan in 50 ml of toluene, 5.8 g of cyclopropane carboxylic acid chloride in 25 ml of toluene was added dropwise at 5°. The mixture was allowed to warm to room temperature and was then refluxed for 15 hours. The solvent was removed in vacuo and the residue partitioned between ether and dilute hydrochloric acid. The ether solution was washed with water and dried. Removal of the solvent in vacuo afforded 4.2 g (99%) of (—)-3-phenoxy-N-cyclopropylcarbonylmorphinan. For analysis, a sample of this compound was distilled, bp 230°-240°/0.05 mmHg, $[\alpha]^{25}$ D−173.45° (c 0.99, MeOH).

EXAMPLE 16

(—)-3-Phenoxy-N-cyclopropylmethylmorphinan

To a suspension of 0.4 g of lithium aluminum hydride in 20 ml of anhydrous tetrahydrofuran was added dropwise, 4.6 g (0.011 mol) of (—)-3-phenoxy-N-cyclopropylcarbonylmorphinan in 30 ml of anhydrous tetrahydrofuran over a period of 15 minutes. After the mixture had been refluxed under nitrogen for 16 hours, it was cooled to room temperature and water was added dropwise. The resulting suspension was filtered and the filtrate was concentrated. The residue was partitioned between ether and 4 N hydrochloric acid. The acidic phase was made basic with concentrated ammonium hydroxide and the aqueous suspension was extracted with ether. The ether solution was washed with water and dried. Removal of the ether under reduced pressure afforded 2.6 g (59%) of the product (—)-3-phenoxy-N-cyclopropylmethylmorphinan. For analysis, a sample of this compound was distilled, bp 190°200°/0.1 mmHg, $[\alpha]^{25}$ D−89.07° (c 0.99, MeOH).

The above product, 2.6 g (0.007 mol), on treatment with hydrogen chloride (anhydrous) in ether afforded the crude hydrochloride, which after crystallization from ethyl acetate gave 1.4 g (50%) of (—)-3-phenoxy-N-cyclopropylmethylmorphinan hydrochloride, mp 186°-188°, $[\alpha]^{25}$ D−67.16° (c 1.00, MeOH).

EXAMPLE 17

(—)-1-(p-Hydroxybenzyl)-2-methyl-1,2,3,4,5,6,7,8-octahydroisoquinoline

A mixture of 253.9 g (0.935 mol) of (—)-1-(p-methoxybenzyl)-2-methyl-1,2,3,4,5,6,7,8-octahydroisoquinoline and 1.2 l. of diethylene glycol was warmed to 80°-100° and 260 g of potassium hydroxide (85 % A.C.S. grade) was added. The reaction mixture was heated to 210° and stirred at this temperature under a constant stream of nitrogen for 36 hours. During this period, time to time the stop cock was removed to allow escape of water vapor. If this is not done, the desired inner temperature of 210° cannot be attained. The dark brown solution was cooled to room temperature and diluted with water (600 ml) and extracted with ether (400 ml). The aqueous solution was made acidic with concentrated aqueous hydrochloric acid and then basified with concentrated aqueous ammonium hydroxide. The aqueous suspension was extracted with ethyl acetate (4×250 ml). The ethyl acetate solution was washed with water and dried. Removal of the solvent gave 172.5 g (72%) of crude (—)-1-(p-hydroxybenzyl)-2-methyl-1,2,3,4,5,6,7,8-octahydroisoquinoline. For analysis, a sample of this compound was recrystallized from tetrahydrofuran-heptane, mp 119°-120°, $[\alpha]^{25}$ D −36.01° (c 0.98, MeOH).

EXAMPLE 18

(—)-1-(p-Phenoxybenzyl)-2-methyl-1,2,3,4,5,6,7,8-octahydroisoquinoline

A solution of 2.4 g (0.009 mol) of (—)-1-(p-hydroxybenzyl-2-methyl-1,2,3,4,5,6,7,8-octahydroisoquinoline, 10 ml of freshly distilled pyridine was refluxed with stirring under nitrogen with 3.1 g of bromobenzene, 2.0 g of potassium carbonate, and 0.1 g of copper (granual) for 9 days. The mixture was filtered and the filtrate was concentrated under reduced pressure. To the residue, ether (150 ml) was added and the ether insoluble material was removed by filtration. The filtrate was extracted with 2 N sodium hydroxide, washed with water, and dried. Removal of the solvent gave 1.18 g (38%) of the product (—)-(p-phenoxybenzyl)-2-methyl-1,2,3,4,5,6,7,8-octahydroisoquinoline (20). For analysis, a sample of this compound was distilled, bp 120°/0.15 mmHg, $[\alpha]^{25}$ D −18.53° (c 1.14, MeOH).

To the above product, 1.0 g (0.003 mol), in 5 ml of ether, a solution of 0.3 g of oxalic acid in ether was added. The crude oxalate was recrystallized from ethanol to give 0.581 g (46%) of (—)-1-(p-phenoxybenzyl)-2-methyl-1,2,3,4,5,6,7,8-octahydroisoquinoline oxalate, mp 160°-162°, $[\alpha]^{25}$ D −37.17° (c 1.00, MeOH).

EXAMPLE 19

Acid catalyzed cyclization of (—)-1-(p-phenoxybenzyl)-2-methyl-1,2,3,4,5,6,7,8-octahydroisoquinoline A mixture of 0.5 g. (0.002 mol) of (—)-1-(p-phenoxybenzyl)-2-methyl-1,2,3,4,5,6,7,8-octahydroisoquinoline and 5 ml. of 99% phosphoric acid was heated at 135° with stirring under nitrogen for 3 days. The reaction mixture was pored onto ice-water and made basic with concentrated ammonium hydroxide. The aqueous suspension was extracted with chloroform. The combined chloroform extracts were washed with water, dried and removal of the solent gave 0.15 g. (30%) of crude (—)-3-phenoxy-N-methylmorphinan.

EXAMPLE 20

(—)-3-Phenoxy-N-cyclobutylcarbonylmorphinan

To a solution of 3.9 g. (0.011 mol) of (—)-3-phenoxy-N-methylmorphinan in 50 ml. of toluene 6.9 g. of cyclobutane carboxylic acid chloride in 30 ml. of toluene was added dropwise at room temperature. The mixture was stirred at this temperature for 1 hour, followed by heating at reflux for 12 days. The reaction mixture was cooled to room temperature and washed successively with 4 N hydrochloric acid, water and 5 N sodium hydroxide. The organic phase was dried and filtered. Removal of the solvent in vacuo afforded 2.3 g. (49%) of (—)-3-phenoxy-N-cyclobutylcarbonylmorphinan. For analysis, a sample of this compound was distilled, b.p. 220° (0.1 mmHg), $[\alpha]_D^{25} = -163.25°$ (c 0.98, MeOH).

EXAMPLE 21

(—)-3-Phenoxy-N-cyclobutylmethylmorphinan

To a suspension of 0.4 g. of lithium aluminum hydride in 40 ml. of anhydrous tetrahydrofuran was added dropwise, 2.1 g. (0.005 mol) of (—)-3-phenoxy-N-cyclobutylcarbonylmorphinan in 20 ml. of anhydrous tetrahydrofuran. After the mixture had been refluxed under nitrogen for 3 hours, it was cooled to room temperature and water was added dropwise. The resulting suspension was filtered and the filtrate was concentrated. The residue was dissolved in ether (50 ml.) and extracted with 4 N hydrochloric acid (75 ml.). The aqueous solution was basified with 10 N sodium hydroxide and extracted with ether (75 ml.). The ethereal solution was washed with water and dried. Removal of the solvent in vacuo gave 1.2 g. (59%) of crude base (—)-3-phenoxy-N-cyclobutylmethylmorphinan. For analysis, a sample of this compound was distilled, b.p. 215°-225° (0.5 mmHg), $[\alpha]_D^{25} = -73.25°$ (c 0.99, MeOH).

The above base, 1.1 g. (0.003 mol), on treatment with hydrogen chloride (anhydrous) in ethyl acetate, afforded the crude hydrochloride which after crystallization from ethyl acetate gave 1.2 g. (100%) of pure (—)-3-phenoxy-N-cyclobutylmethylmorphinan hydrochloride, m.p. 175°-177°, $[\alpha]_D^{25} = -66.59°$ (c 1.03, MeOH).

EXAMPLE 22

(—)-3-Phenoxy-N-phenylacetylmorphinan

To a mixture of 4.0 g. (0.012 mol) of (—)-3-phenoxymorphinan, 2.5 g. of triethylamine and 15 ml. of methylene chloride was added dropwise a solution of 2.9 g. of phenyl acetyl chloride in 15 ml. of methylene chloride. After the mixture had been refluxed for 14 hours, it was cooled to room temperature and washed successively with water, 4 N hydrochloric acid, 2 N sodium hydroxide and water. The organic solution was dried and the solvent was evaporated to give 4.4 g. (80%) of the crude base (—)-3-phenoxy-N-phenylacetylmorphinan. For analysis, a sample of this compound was distilled, b.p. 240°-250° (0.05 mmHg), $[\alpha]_D^{25} = 133.27°$ (c 1.11, MeOH).

EXAMPLE 23

(—)-3-Phenoxy-N-phenethylmorphinan

To a suspension of 0.8 g. of lithium aluminum hydride in 40 ml. of anhydrous tetrahydrofuran was added dropwise, 4.2 g. (0.01 mol) of (—)-3-phenoxy-N-phenylacetylmorphinan in 40 ml. of anhydrous tetrahydrofuran over a period of 45 minutes. After the mixture had been refluxed under nitrogen for 3 hours, it was cooled to room temperature and water was added dropwise. The resulting suspension was filtered and the filtrate was concentrated. The residue was partitioned between ether and water. The ethereal solution was dried and the solvent was evaporated to give 3.5 g. (86%) of the crude base (—)-3-phenoxy-N-phenethylmorphinan. For analysis, a sample of this compound was distilled, b.p. 160°-165° (0.1 mmHg), $[\alpha]_D^{25} = -100.27°$ (c 0.55, MeOH).

To the above base, 3.2 g. (0.007 mol) in ether, a solution of 0.8 g. of oxalic acid in ether was added. The crude oxalate was recrystallized twice from ethanol to give 1.7 g. (39%) pure (—)-3-phenoxy-N-phenethylmorphinan oxalate, m.p. 217°-219°, $[\alpha]_D^{25} = -72.17°$ (c 1.06, MeOH).

EXAMPLE 24

(—)-3-Phenoxy-N-[(2-furylmethyl)carbonyl]morphinan

To a mixture of 4.0 g. (0.012 mol) of (—)-3-phenoxymorphinan,2.5 g. of triethylamine and 15 ml. of methylene chloride was added dropwise a solution of 2.7 g. of 2-furyl acetyl chloride. After the mixture had been refluxed for 14 hours, it was cooled to room temperature, and washed successively with water, 4 N hydrochloric acid, 5 N sodium hydroxide and water. The organic solution was dried and the solvent was evaporated to give 5.2 g. (97%) of crude (—)-3-phenoxy-N-[(2-furylmethyl)carbonyl]-morphinan. For analysis, a sample of this compound was distilled, b.p. 215°-225° (0.1 mmHg), $[\alpha]_D^{25} = -135.36°$ (c 1.06, MeOH).

EXAMPLE 25

(—)-3-Phenoxy-N-[2-(2-furyl)ethyl]morphinan

To a suspension of 0.8 g. of lithium aluminum hydride in 40 ml. of anhydrous tetrahydrofuran was added dropwise, 5.1 g. (0.012 mol) of (—)-3-phenoxy-N-[(2-furylmethyl)carbonyl]morphinan in 40 ml. of anhydrous tetrahydrofuran. After the mixture had been refluxed under nitrogen for 3 hours, it was cooled to room temperature and water was added dropwise. The resulting suspension was filtered and the filtrate was concentrated. The residue was partitioned between ether and water. The ethereal solution was washed with 5 N sodium hydroxide and dried. Removal of the solvent in vacuo gave an oily residue (2.8 g.). The residue was purified by chromatography over silica gel (50 g.) and elution with ether gave 1.3 g. (26%) of the base (—)-3-phenoxy-N-[2-(2-furyl)ethyl])morphinan. For analysis, a sample of this compound was distilled, b.p. 145°-150° (0.1 mmHg), $[\alpha]_D^{25} = -94.15°$ (c 1.06, MeOH).

To the above base, 1.2 g. (0.003 mol) in ether, a solution of 0.3 g. of oxalic acid in ether was added. The crude oxalate was recrystallized twice from ethanol to give 1.0 g. (68%) of (—)-3-phenoxy-N-[2-(2-furyl)ethyl]morphinan oxalate, m.p. 195°-197° (d), $[\alpha]_D^{25} = -64.52°$ (c 1.03, MeOH).

EXAMPLE 26

(—)-3-Phenoxy-N-[(2-thienylmethyl)carbonyl]morphinan

To a mixture of 4.0 g (0.012 mol) of (—)-3-phenoxymorphinan, 2.5 g. of triethylamine and 15 ml. of methylene chloride was added dropwise a solution of 3.3 g. of 2-thienyl acetyl chloride in 15 ml. of methylene chloride. After the mixture had been refluxed for 15 hours, it was cooled to room temperature, diluted with methylene chloride and washed successively with water, 4 N hydrochloric acid, 5 N sodium hydroxide and water. The organic phase was dried and the solvent was evaporated to give 5.5 g. (100%) of the crude base (—)-3-phenoxy-N-[(2-thienylmethyl)carbonyl]morphinan. For analysis, a sample of this compound was distilled. b.p. 235°-240° (0.05 mmHg), $[\alpha]_D^{25} = -134.17°$ (c 1.03, MeOH).

EXAMPLE 27

(—)-3-Phenoxy-N-[2-(2-thineyl)ethyl]morphinan

To a suspension of 0.8 g of lithium aluminum hydride in 40 ml. of anhydrous tetrahydrofuran was added dropwise 6.2 g. (0.014 mol) of (—)-3-phenoxy-N-[2-thienylmethyl)carbonyl]morphinan in 40 ml. of anhydrous tetrahydrofuran. After the mixture had been refluxed under nitrogen for 3 hours, it was cooled to room temperature and water was added dropwise. The resulting suspension was filtered and the filtrate was concentrated. The residue was dissolved in ether and the ethereal solution was extracted with 4 N hydrochloric acid. The aqueous phase was basified with 10 N sodium hydroxide and extracted with ether. The organic phase was dried and the solvent was removed in vacuo to give 3.3 g. (55%) of crude base(—)-3-phenoxy-N-[2-(2-thienyl)ethyl]morphinan. For analysis, a sample of this compound was distilled, b.p. 150° (0.05 mmHg), $[\alpha]_D^{25} = -96.45°$ (c 1.23, MeOH).

The above base, 3.0 g. (0.007 mol) in ether was treated with sulfuric acid. The crude sulfate was recrystallized from methanol-ether to give 1.8 g. (49%) of pure (—)-3-phenoxy-N-[2-(2-thienyl)ethyl]morphinan sulfate, m.p. 135°-138°, $[\alpha]_D^{25} = -67.28°$ (c 1.00, MeOH).

EXAMPLE 28

(—)-3-(m-Fluoro)phenoxy-N-methylmorphinan

A mixture of 3.0 g. (0.011 mol) of (—)-3-hydroxy-N-methylmorphinan, 50 ml. of freshly distilled pyridine, 2.2 g. of 3-bromofluorobenzene, 2.4 g. of potassium carbonate and 3.0 g. of copper (granular) were heated in a stainless steel container at 120° for 8 days. After cooling, the container was opened and the mixture was filtered. The filtrate was concentrated under reduced pressure and the residue was partitioned between ether and 10 N sodium hydroxide. The ether solution was washed with water and dried. Removal of the solvent in vacuo gave a dark residue which was distilled, b.p. 131°-140° (0.15 mmHg) to afford 0.5 g. (13%) of the base (—)-3-(m-fluoro)phenoxy-N-methylmorphinan, $[\alpha]_D^{25} = -56.79°$ (c 1.04, MeOH).

To the above base, 0.4 g. (0.001 mol) in 2 ml. of acetone, a solution of 0.2 g. of d-tartaric acid in 10 ml. of acetone was added. The crude tartrate was recrystallized from acetone to give 0.41 g. (71%) of (—)-3-(m-fluoro)phenoxy-N-methylmorphinan d-tartrate hemihydrate, m.p. 121°-123°, $[\alpha]_D^{25} = -18.61°$ (c 1.03, MeOH).

EXAMPLE 29

(—)-3-(o-Methoxy)phenoxy-N-cyclopropylmethylmorphinan

To a solution of 1.7 g. (0.005 mol) of (—)-3-(o-methoxy)phenoxy-N-methylmorphinan in 25 ml. of toluene, 2.5 g. of cyclopropane carboxylic acid chloride in 15 ml. of toluene was added dropwise under nitrogen at room temperature. The reaction mixture was refluxed for 13 days and the solvent was removed in vacuo. The residue was partitioned between ether (500 ml.) and 4 N hydrochloric acid (200 ml.). The ethereal solution was washed with dilute ammonium hydroxide then with water and dried. Removal of the solvent gave 1.4 g. (71%) of the crude base (—)-3-(o-methoxy)-phenoxy-N-cyclopropylcarbonylmorphinan, which was reduced without further purification.

To a suspension of 0.2 g. of lithium aluminum hydride in 20 ml. of anhydrous tetrahydrofuran was added dropwise 1.0 g. (0.002 mol) of (—)-3-(o-methoxy)phenoxy-N-cyclopropylcarbonylmorphinan in 10 ml. of anhydrous tetrahydrofuran. After the mixture had been refluxed under nitrogen for 15 hours, it was cooled to room temperature and water was added dropwise. The resulting suspension was filtered and the filtrate was concentrated. The residue was partitioned between ether and 4 N hydrochloric acid. The aqueous solution was basified with 10 N sodium hydroxide and extracted with ether. The ethereal solution was washed with water and dried. Removal of the solvent in vacuo gave 0.7 g. (725) of crude base (—)-3-(o-methoxy)phenoxy-N-cyclopropylmethylmorphinan. For analysis, a sample of this compound was distilled, b.p. 210°-220° (0.1 mmHg), $[\alpha]_D^{25} = -57.34°$ (c 0.52, MeOH).

The above base, 0.5 g. (0.001 mol) on treatment with hydrogen chloride (anhydrous) in ethyl acetate afforded the crude hydrochloride, which after crystallization from ethanol-ether gave 0.363 g. (67%) of (—)-3-(o-methoxy)phenoxy-N-cyclopropylmethylmorphinan hydrochloride, m.p. 226°-227° (d), $[\alpha]_D^{25} = -71.18°$ (c 1.00, MeOH).

EXAMPLE 30

(—)-3-(p-Methoxy)phenoxy-N-cyclopropylmethylmorphinan

To a solution of 1.9 g. (0.005 mol) of (—)-3-(p-methoxy)phenoxy-N-methylmorphinan in 25 ml. of toluene, 2.9 g. of cyclopropane carboxylic acid chloride in 12 ml. of toluene was added dropwise under nitrogen at room temperature. The reaction mixture was stirred at reflux temperature for 13 days and the solvent was removed under reduced pressure. The residue was partitioned between ether and 4 N hydrochloric acid. The ethereal solution was washed with dilute ammonium hydroxide, then water and dried. Removal of the solvent gave an oily residue which was distilled to give 1.2 g. (56%) of (—)-3-(p-methoxy)phenoxy-N-cyclopropylcarbonylmorphinan, b.p. 170° (0.05 mmHg). This compound was used for the reaction without further purification.

To a suspension of 0.4 g. of lithium aluminum hydride in 20 ml. of anhydrous tetrahydrofuran was added dropwise 2.2 g (0.005 mol) of (—)-3-(p-methoxy)phenoxy-N-cyclopropylcarbonylmorphinan in 10 ml. of anhydrous tetrahydrofuran. After the mixture had been refluxed under nitrogen for 15 hours, it was cooled to room temperature and water was added dropwise. The resulting suspension was filtered and the filtrate was concentrated. The residue was partitioned between ether and 4 N hydrochloric acid. The aqueous solution was made basic with 10 N sodium hydroxide and extracted with ether. The etheral solution was washed with water and dried. Removal of the solvent in vacuo gave 1.75 g. (825) of the crude base (—)-3-(p-methoxy)phenoxy-N-cyclopropylmethylmorphinan. For analysis, a sample of this compound was distilled, b.p. 215°-220° (0.25 mmHg), $[\alpha]_D^{25} = -77.78°$ (c 0.45, MeOH).

The above base, 1.5 g. (0.004 mol) on treatment with hydrogen chloride (anhydrous) in ethyl acetate afforded the crude hydrochloride. Recrystallization from ethanol-ether gave 1.27 g. (795) of (—)-3-(p-methoxy)-phenoxy-N-cyclopropylmethylmorphinan hydrochloride, m.p. 204°-206°, $[\alpha]_D^{25} = -60.50°$ (c 0.99, MeOH).

EXAMPLE 31

Tablet was formulated as follows:

| Item | Ingredient | mg/tablet |
|---|---|---|
| 1. | (−)-3-phenoxy-N-methyl morphinan | 5.0 |
| 2. | Lactose | 99.0 |
| 3. | Pregelatinized starch | 10.0 |
| 4. | Corn Starch | 15.0 |
| 5. | Modified Starch | 10.0 |
| 6. | Magnesium stearate | 1.0 |
| | Weight of tablet | 140 mg |

Procedure

1. Mix items 1, 2, 3, 4 and 5 in a suitable mixer, granulate with water. Dry over night in an oven. Mill through a Fitzpatrick mill.
2. Mix with item 6 and compress on a suitable press.

EXAMPLE 32

A tablet was formulated as follows:

| Item | Ingredient | mg/tablet |
|---|---|---|
| 1. | (−)-3-phenoxy-N-methyl-morphinan | 10.0 |
| 2. | Lactose anhydrous | 103.0 |
| 3. | Avicel | 45.0 |
| 4. | Modified starch | 10.0 |
| 5. | Corn starch | 30.0 |
| 6. | Magnesium stearate | 2.0 |
| | Weight of tablet | 200 mg |

Procedure

1. Mix items 1, 2, 3, 4 and 5 in a suitable mixer for 10 to 15 minutes.
1. Add magnesium stearate (item 6) as a premix and mix for 4 minutes. Compress on a suitable press.

EXAMPLE 33

A capsule Formulation

| Item | Ingredient | mg/capsule |
|---|---|---|
| 1. | (−)-3-phenoxy-N-methyl-morphinan | 10.0 |
| 2. | Lactose | 218.0 |
| 3. | Corn Starch | 50.0 |
| 4. | Magnesium stearate | 2.0 |
| 5. | Talc | 10.0 |
| | Fill weight of capsule | 220 mg |

Procedure

1. Mix items 1, 2 and 3 in a suitable mixer. Mill through suitable mill.
2. Mix with items 4 and 5 and fill on capsule machine.

EXAMPLE 34

A capsule was formulated as follows:

| Item | Ingredient | mg/capsule |
|---|---|---|
| 1. | (−)-3-(p-methoxy)phenoxy-N-methyl-morphinan | 25.0 |
| 2. | Lactose | 257.0 |
| 3. | Corn Starch | 70.0 |
| 4. | Magnesium stearate | 3.0 |
| 5. | Talc | 15.0 |
| | Fill weight of capsule | 370 mg. |

Procedure:

1. Mix items 1, 2 and 3 in a suitable mixer. Mill through suitable mill.

2. Mix with items 4 and 5 and fill on capsule machine.

EXAMPLE 35

A capsule was formulated in the manner of Example 34 except the active ingredient was (—)-(p-methyl)-phenoxy-N-methylmorphinan.

EXAMPLE 36

A tablet was formulated (Wet Granulation) as follows

| Item | Ingredients | mg/tablet |
|---|---|---|
| 1. | (—)-3-(p-methoxy)phenoxy-N-methylmorphinan | 0.5 |
| 2. | Lactose | 186.5 |
| 3. | Modified starch | 35 |
| 4. | Pregelatinized starch | |
| 5. | Distilled water qs | — |
| 6. | Magnesium Stearate | 4 |
| | Weight of tablet | 250 mg |

Procedure:

1. Mix items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 37

A tablet (Wet granulation) was formulated as follows:

| Item | Ingredients | mg/tablet |
|---|---|---|
| 1. | (—)-3-pentafluorophenoxy-N-methylmorphinan | 2.0 |
| 2. | Lactose | 253.0 |
| 3. | Modified starch | 55 |
| 4. | Pregelatinized starch | 35 |
| 5. | Distilled water qs | — |
| 6. | Magnesium Stearate | 5 |
| | Weight of tablet | 350 mg |

Procedure:

1. Mix Items 1–4 in a suitable mixer.
2. Granulate with sufficient distilled water to proper considtency. Mill.
3. Dry in a suitable oven.
4. Mill and mix with magnesium stearate for 3 minutes.
5. Compress on a suitable press equipped with appropriate punches.

I claim:

1. A compound of the formula

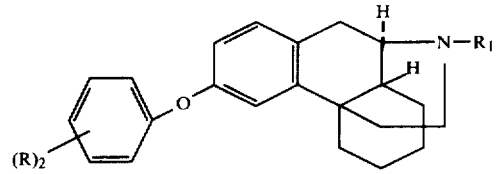

wherein R is halo, lower alkyl, lower alkoxy, hydroxy, nitro or hydrogen; $R_1$ is hydrogen, lower alkenyl containing from 2 to 7 carbon atoms, $—CH_2—(CH_2)_pR_2$, and $$—\overset{O}{\overset{\|}{C}}—(CH_2)_pR_2;$$

$R_2$ is phenyl, cyclo-lower alkyl containing from 3 to 6 carbon atoms, or a 5 or 6 membered heteroaromatic ring containing a hetero atom selected from the group consisting of oxygen, nitrogen and sulfur; p is an integer from 0 to 3; and n is an integer from 1 to 5; and the lower alkoxy and lower alkyl substituents contain from 1 to 7 carbon atoms and pharmaceutically acceptable salts thereof.

2. The compound of claim 1 wherein $R_1$ is lower alkyl.

3. The compound of claim 2 wherein said compound is (—)-3-phenoxy-N-methylmorphinan.

4. The compound of claim 2 wherein R is halo.

5. The compound of claim 4 wherein said compound is (—)-3-pentafluorophenoxy-N-methylmorphinan.

6. The compound of claim 4 wherein said compound is(—)-3-(p-fluoro)phenoxy-N-methylmorphinan.

7. The compound of claim 2 wherein R is nitro.

8. The compound of claim 7 wherein said compound is (—)-3-(o-nitro)-phenoxy-N-methyl-morphinan.

9. The compound of claim 2 wherein R is hydroxy.

10. The compound of claim 9 wherein said compound is (—)-3-(p-hydroxy)phenoxy-N-methylmorphinan.

11. The compound of claim 2 wherein R is lower alkoxy.

12. The compound of claim 11 wherein said compound is (—)-3-(o-methoxy)phenoxy-N-methylmorphinan.

13. The compound of claim 1 wherein $R_1$ is $—CH_2—(CH_2)_p—R_2$.

14. The compound of claim 13 wherein said compound is (—)-3phenoxy-N-cyclopropylmethylmorphinan.

15. The compound of claim 13 wherein $R_1$ is $$—\overset{O}{\overset{\|}{C}}—(CH_2)_p—R_2.$$

16. The compound of claim 13 wherein said compound is (—)-3-phenoxy17-cyclopropylcarbonylmorphinan.

17. A compound of the formula

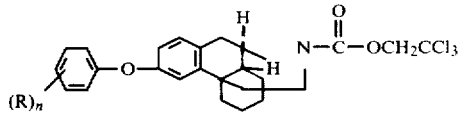

wherein R is halo, nitro, lower alkyl, lower alkoxy, hydroxy or hydrogen and n is an integer from 1 to 5.

18. The compound of claim 17 wherein said compound is (—)-3-phenoxyN-trichlorocarbethoxymorphinan.

* * * * *